United States Patent [19]
Zalipsky

[11] Patent Number: 5,808,096
[45] Date of Patent: Sep. 15, 1998

[54] PROCESS FOR PREPARING ACTIVE CARBONATES OF POLYALKYLENE OXIDES FOR MODIFICATION OF POLYPEPTIDES

[75] Inventor: Shmuel Zalipsky, Edison, N.J.

[73] Assignee: Enzon, Inc., Piscataway, N.J.

[21] Appl. No.: 785,320

[22] Filed: Jan. 21, 1997

Related U.S. Application Data

[62] Division of Ser. No. 198,193, Feb. 17, 1994, Pat. No. 5,612,460, and a division of Ser. No. 817,757, Jan. 8, 1992, Pat. No. 5,324,844, which is a division of Ser. No. 511,243, Apr. 19, 1990, Pat. No. 5,122,614, which is a continuation-in-part of Ser. No. 340,928, Apr. 19, 1989, abandoned.

[51] Int. Cl.$^6$ ........................ C07D 207/40; C07D 207/46
[52] U.S. Cl. ........................................ 548/520; 548/542
[58] Field of Search ........................ 548/520, 542

[56] References Cited

U.S. PATENT DOCUMENTS

| | | | |
|---|---|---|---|
| 4,179,337 | 12/1979 | Davis et al. | 435/181 |
| 4,248,786 | 2/1981 | Batz et al. | 260/326.26 |
| 4,609,546 | 9/1986 | Hiratani | 514/2 |
| 4,714,768 | 12/1987 | Henklein et al. | 548/435 |
| 4,891,430 | 1/1990 | Barcelo et al. | 548/542 X |
| 4,902,502 | 2/1990 | Witeche et al. | 424/83 |
| 5,006,333 | 4/1991 | Saifer et al. | 435/181 |
| 5,081,295 | 1/1992 | Reardan et al. | 435/177 |
| 5,122,614 | 6/1992 | Zalipsky | 548/520 |
| 5,185,368 | 2/1993 | Peter et al. | 514/476 |
| 5,214,131 | 5/1993 | Sano et al. | 530/345 |
| 5,219,564 | 6/1993 | Zalipsky et al. | 530/391.9 |
| 5,235,028 | 8/1993 | Barany et al. | 528/335 |
| 5,252,714 | 10/1993 | Harris et al. | 530/391.9 |
| 5,281,698 | 1/1994 | Nitecki | 530/409 |
| 5,286,637 | 2/1994 | Veronese et al. | 435/68.1 |

FOREIGN PATENT DOCUMENTS

| | | |
|---|---|---|
| 0134041 | 3/1985 | European Pat. Off. . |
| 246539 | 6/1987 | Germany . |
| 260701 | 10/1988 | Germany . |
| 261791 | 11/1988 | Germany . |
| 279486 | 6/1990 | Germany . |
| 9013540 | 11/1990 | WIPO . |

OTHER PUBLICATIONS

Matsuda et al, Chemical Abstracts. vol. III (1979).110246 m.
Abuchowski, et al. *Cancer Biochem. Biophys.* 1984; 7:175–186.
Matsuda, et al. *Chem Abstracts* 1989; 111:112046m.
Abuchowski, et al., Cancer Biochem Biophys. 1984; 7: 175–178 (Exhibit D).
Drobnik, J. et al., *Biotechnology and Bioengineering.* 1982; vol. 24: 487–493.
Miron, T. et al., *Methods in Enzymology.* 1987; vol. 135: 84–90.
Wilchek, M. et al. "Activation of Sepharose with N,N'—Disuccinimidyl Carbonate" Applied Biochemistry and Biotechnology vol. 11 pp. 191–193 (1985).
Ogura, H. et al. "A Novel Active Ester Synthesis Reagent (N,N'—Disuccinimidyl Carbonate)" Tetrahedron Letters No. 49 pp. 4745–4746 (1979).
Veronese et al, *Applied Biochemistry and Biotechnology,* vol. 11, No. 2, pp. 141–152, Apr. 1985.
Wichek et al, *Applied Biochemistry and Biotechnology,* vol. II, pp. 191–193, 1985.
Veronese et al, *Applied Biochemistry and Biotechnology,* vol. 11, No. 2, pp. 141–152, Apr. 1985.
Zalipsky *Chemical Abstracts,* vol. 108, p. 719, Ref. #205057d, 1988, (Dics. Abst. Inst. B 1758.48(8) 2329).
Nagae et al., *Jinko Zoki,* vol. 18(1), 137–40 (1989).

*Primary Examiner*—Jeffrey Stucker
*Assistant Examiner*—Hankyel T. Park
*Attorney, Agent, or Firm*—Roberts & Mercanti, L.L.P.

[57] ABSTRACT

Poly(ethylene glycol)-N-succinimide carbonate and its preparation are disclosed. Polyethylene glycol (PEG) is converted into its N-succinimide carbonate derivative. This form of the polymer reacts readily with amino groups of proteins in aqueous buffers. The modified proteins have PEG-chains grafted onto the polypeptide backbone by means of stable, hydrolysis-resistant urethane (carbamate) linkages.

14 Claims, 3 Drawing Sheets

Hours of incubation at 37 °C

—●— SS-PEG conjugate, 0.1M phosphate, pH 7.8
—○— SS-PEG conjugate, 50mM PBS, pH 7.4
—■— SS-PEG conjugate, 0.1M borate, pH 8.5
—□— SC-PEG conjugate, 0.1M borate, pH 8.6

PROCESS FOR PREPARING ACTIVE CARBONATES OF POLYALKYLENE OXIDES FOR MODIFICATION OF POLYPEPTIDES

This application is a division of application Ser. No. 08/198,193 filed Feb. 17, 1994. now U.S. Pat. No. 5,612,460 and in turn is a division of Ser. No. 08/817,757 filed Jan. 8, 1992, U.S. Pat. No. 5,324,844, which in turn is a division of Ser. No. 07/511,243 filed Apr. 19, 1990 U.S. Pat. No. 5,122,614 which is a continuation-in-part of Ser. No. 07/340,928, Apr. 19, 1989, now abandoned.

BACKGROUND OF THE INVENTION

The present invention relates to chemical modification of polypeptides by means of covalent attachment of strands of polyalkylene oxide to a polypeptide molecule such as is disclosed in U.S. Pat. No. 4,179,337, to Davis, et al. It is disclosed in Abuchowski & Davis "Enzymes as Drugs", Holcenberg & Roberts, eds., pp. 367–383, John Wiley & Sons, N.Y. (1981) that such preparations of polypeptides have reduced immunogenicity and antigenicity and also have a longer lifetime in the bloodstream as compared to the parent polypeptides. These beneficial properties of the modified polypeptides make them very useful in a variety of therapeutic applications, such as enzyme therapy.

The active groups that are introduced onto polyalkylene oxides for the purpose of subsequent attachment of these polymers to proteins must satisfy the following requirements:

1. The active groups have to be reactive enough to afford fast reaction with a protein under mild conditions;
2. The residues released from the active groups during the process of modification have to be non-toxic and/or readily separable from the protein-polymer adduct.

To effect covalent attachment of polyethylene glycol (PEG) to a protein, the hydroxyl end-groups of the polymer must first be converted into reactive functional groups. This process is frequently referred to as "activation" and the product is called "activated PEG". Methoxypolyethylene glycol (mPEG) derivatives, capped on one end with a functional group, reactive towards amines on a protein molecule, are used in most cases.

The most common form of activated PEG heretofore used for preparation of therapeutic enzymes is poly(ethylene glycol) succinoyl-N-hydroxysuccinimide ester (SS-PEG) [Abuchowski, et al. Cancer Biochem. Biophys. 7, 175–186 (1984), Scheme 1]. Use of this activated polymer satisfies both of the requirements listed above. However, it has one major drawback. The ester linkage between the polymer and succinic acid residue has limited stability in aqueous media [U.S. Pat. No. 4,670,417, to Iwasaki, et al. (1987); Ulbrich, et al., Makromol. Chem. 187, 1131–1144 (1986)].

Scheme 1: Conventional attachment of PEG to a protein using SS-PEG as the activated form of the polymer

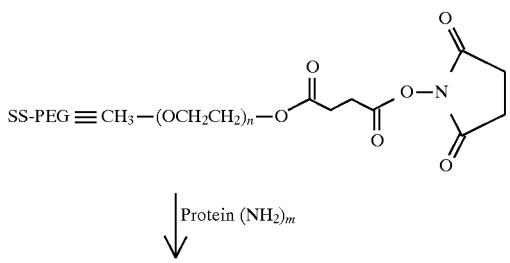

-continued
Scheme 1: Conventional attachment of PEG to a protein using SS-PEG as the activated form of the polymer

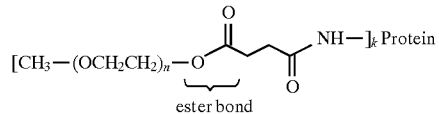

Various functionalized polyethylene glycols (PEG) have been effectively used in such fields as protein modification (Abuchowski & Davis, 1981, supra), peptide chemistry [Zalipsky, et al., Int. J. Peptide Protein Res., 30, 740–783 (1987)] and preparation of conjugates with biologically active materials [Zalipsky, et al., Eur. Polym. J. 19, 1177–1183 (1983) and Zalipsky and Barany, Polymer Preprints, Am. Chem. Soc. Div. Polym. Chem. 27(1), 1–2 (1986)]. PEG protein conjugates useful in medical applications have shown promise, particularly with regard to their stability to proteolytic digestion, reduced immunological response and longer half-life times in the bloodstream.

To accomplish this, the prior art has activated the hydroxy group of PEG with cyanuric chloride and the resulting compound then coupled with proteins (Abuchowski, et al. (1977) J. Biol. Chem. 252, 3578; Abuchowski and Davis, 1981, supra). However, various disadvantages of using this method exist, such as the toxicity of cyanuric chloride and the non-specific reactivity for proteins having functional groups other than amines, such as free essential cysteine or tyrosine residues.

In order to overcome these and other disadvantages, alternative procedures, such as succinimidyl succinate derivatives of PEG (SS-PEG) have been introduced (Abuchowski, et al. 1984, supra, see Scheme 1, above). It reacts quickly with proteins (30 min) under mild conditions yielding active yet extensively modified conjugates use of this activated polymer has one major disadvantage. The ester linkage between the polymer and the succinic acid residue has limited stability in aqueous media [U.S. Pat. No. 4,670, 417 to Iwasaki, et al. and Ulbrich, et al. Makromol Chem., 187, 1131–1144 (1986)].

Formation of urethane linkages between amino groups of a protein and PEG overcomes the problem of hydrolytic loss of the polymer chains [Veronese, et al., Appl. Biochem. Biotechnol. 11, 141–152 (1985)]. In fact, it was demonstrated on radioactively labeled PEG-derivatives that urethane links are completely stable under a variety of physiological conditions [Larwood & Szoka J., Labeled Compounds Radiopharm., 21, 603–614 (1984)]. The attachment of PEG to a protein via a carbamate derivative was accomplished [Beauchamp, et al. Analyt. Biochem. 131, 25–33 (1983)] using carbonyldiimidazole-activated PEG. However, the polymer activated in this manner is not very reactive and therefore long reaction times (48–72 hrs at pH 8.5) were required to achieve sufficient modifications. Therefore, the carbonyldiimidazole-activated agent clearly does not satisfy the first requirement noted above. An additional disadvantage of this approach is in the relatively high cost of carbonyldiimidazole.

Use of PEG-phenylcarbonate derivatives for preparation of urethane-linked PEG-proteins was reported [see Veronese, et al. (1985), supra]. The main drawback of this approach lies in the toxicity of the hydrophobic phenol residues (p-nitrophenol or 2, 4, 5-trichlorophenol) and their affinity for proteins. Clearly this method does not satisfy the second requirement noted above.

Each of the activated forms of the polymer has properties which can be considered advantageous or disadvantageous, depending on the system of use. In light of the many applications of PEG-polypeptides, it is desirable to broaden the arsenal of protein modifying PEG-reagents made for a specific end use.

SUMMARY OF THE INVENTION

The present invention provides a compound having the structure

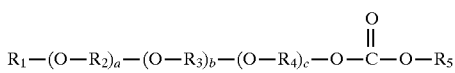

wherein $R_1$ is H—, $H_3C$—, an oxycarbonyl N-dicarboximide group, or any other functional group; wherein each $R_2$, $R_3$, and $R_4$ is an alkyl group which may be straight, branched, disubstituted, or unsubstituted, and wherein each $R_2$, $R_3$, and $R_4$ may be independently the same as, or different from, the others of $R_2$, $R_3$, and $R_4$;

wherein $R_5$ is an N-dicarboximide group; and wherein a is an integer between 1 and 1000 and each of b and c is an integer between 0 and 1000, and the sum of a, b, and c is between 10 and 1000.

The present invention also provides a process for preparing the compound which comprises reacting a compound having the structure

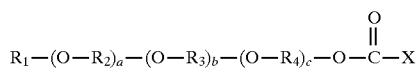

wherein $R_1$ is H—, $H_3C$—, or any other functional group;

wherein each $R_2$, $R_3$, and $R_4$ is an alkyl group which may be straight, branched, disubstituted, or unsubstituted, and wherein each $R_2$, $R_3$, and $R_4$ may be independently the same as, or different from, the others of $R_2$, $R_3$, and $R_4$;

wherein X is a halogen;

wherein a is an integer between 1 and 1000 and each of b and c is an integer between 0 and 1000, and the sum of a, b, and c is between 10 and 1000.

with an N-hydroxydicarboximide in the presence of a base.

The present invention further provides a modified polypeptide comprising a polypeptide having bound thereto at least one polymer having the structure

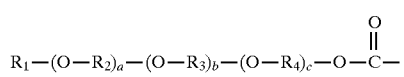

wherein $R_1$ is H—, $H_3C$—, on oxycarbonyl-N-dicarboximide or any other functional group;

wherein each $R_2$, $R_3$, and $R_4$ is an alkyl group which may be straight, branched, substituted, or unsubstituted, and wherein each $R_2$, $R_3$, and $R_4$ may be independently the same as, or different from, the others of $R_2$, $R_3$, and $R_4$.

wherein a is an integer between 1 and 1000 and each of b and c is an integer between 0 and 1000, and the sum of a, b, and c is between 10 and 1000.

wherein each polymer is covalently bound to an amine group of the polypeptide by a urethane linkage.

The invention also provides a process for preparing a modified polypeptide comprising reacting a polypeptide with the compound at a pH in the range of about 5.8–11.

Solutions of both types of PEG-BSA conjugates (~61% modification) at concentration 4 mg/ml (by Bluret assay) were incubated in the appropriate buffer. At given time intervals aliquots of these solutions were injected into an HPLC equipped with Zorbax GF-450 column and RI-detector to quantitate mPEG-5000.

Figure 2:
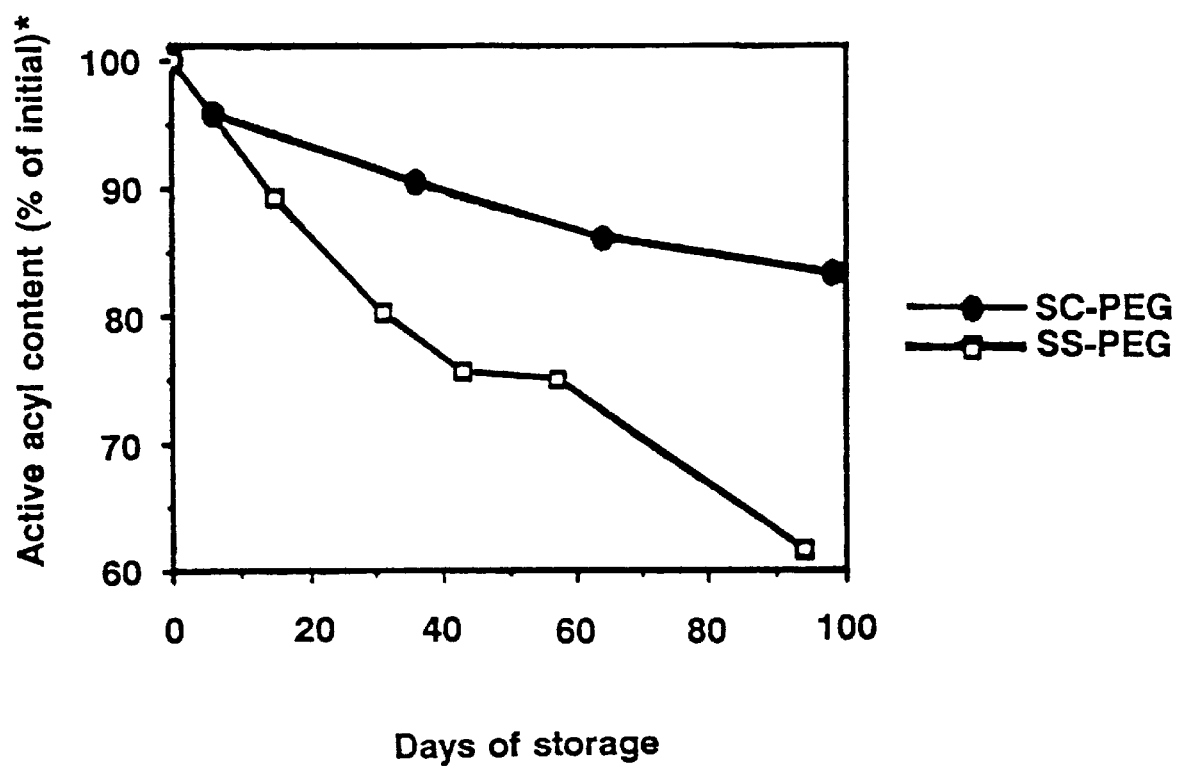

FIG. 2. Stability of SS-PEG and SC-PEG at 22° C. Experimental Conditions

The activated PEG's were stored in the form of fine powder in tightly closed polypropylene containers. At given time intervals samples of each polymer were assayed for active acyl content.

Figure 3:
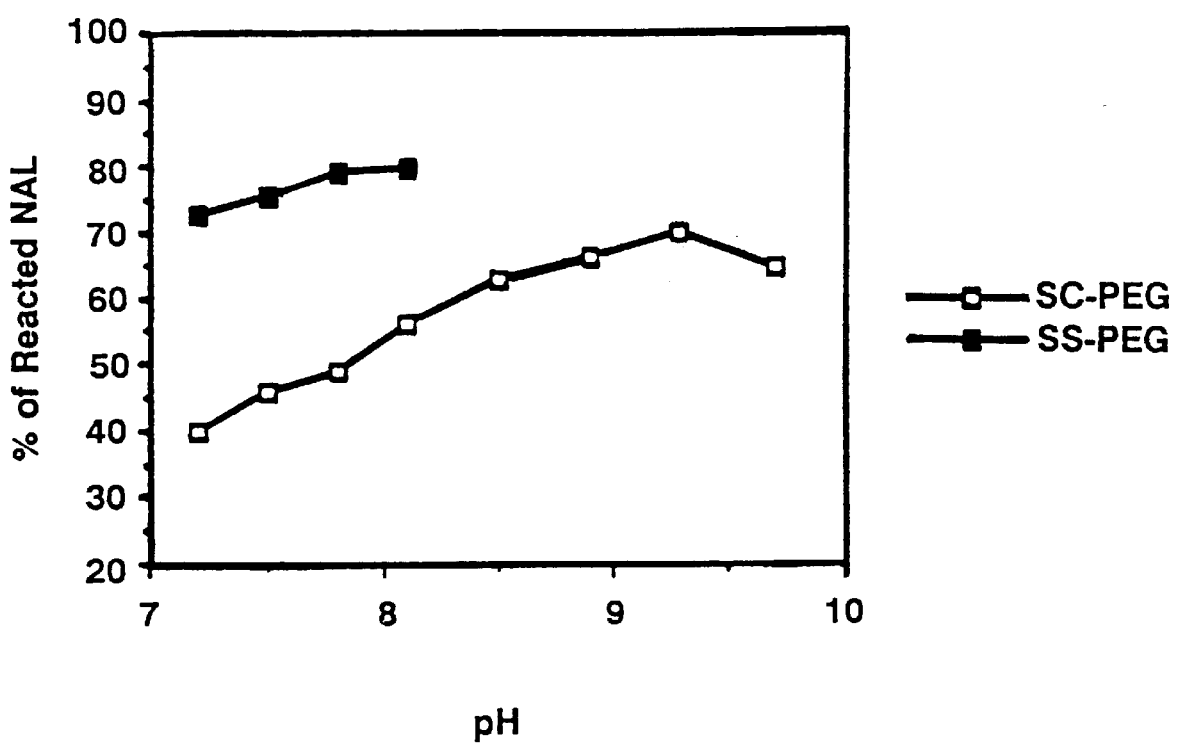

FIG. 3. Reactivity of activated PEG's as a function of pH. Experimental Conditions To triethanolamine-borate buffer (0.3M, 1 ml) at the appropriate pH, stock solution of NAL in water (50 mM, 0.1 ml) was added followed by stock solution of the appropriate activated PEG in $CH_3CN$ (50 mM active acyl, 0.1 ml). The resultant solution was vortexed and incubated at 28° C. for 1 hr. A mixture of the same components but leaving out SX-PEG was used as a control. The TNBS—assay version of Snyder, et al. [(1975) Anal. Biochem. 64, 284] was used to determine the unreacted NAL.

DESCRIPTION OF THE INVENTION

The present invention describes activated polyalkylene oxides having the general structure:

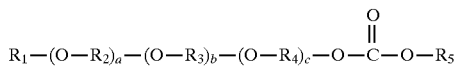

wherein $R_1$ is H—, $H_3C$—, an oxycarbonyl N-dicarboximide group, or any other functional group; wherein each $R_2$, $R_3$, and $R_4$ is an alkyl group which may be straight, branched, disubstituted, or unsubstituted, and wherein each $R_2$, $R_3$ and $R_4$ may be independently the same as, or different from, the others of $R_2$, $R_3$, and $R_4$; wherein $R_5$ is an N-dicarboximide group; and wherein a is an integer between 1 and 1000 and each of b and c is an integer between 0 and 1000, and the sum of a, b, and c is between 10 and 1000.

More specifically, the invention relates to preparation and use of a new, activated PEG, namely, poly(ethylene glycol) -succinidyl carbonate (SC-PEG) and the bifunctional derivative of PEG, namely, polyethylene glycol-bis-succinidyl carbonate (BSC-PEG). Furthermore, heterobifunctional derivatives of PEG are possible (Zalipsky and Barany, supra); one of the end groups is succinidyl carbonate and the other end group ($R^1$, see Scheme 2, infra) contains a different reactive functional group, such as a free carboxyl group or an amine acid. These materials react readily with amino groups of proteins to afford PEG attachment through stable urethane linkages (Scheme 2, below). The reactivity of the new agents, SC-PEG and BSC-PEG, are comparable to the conventionally used SS-PEG. Thus, high degrees of modification are achievable in mild conditions (aqueous buffers, pH 5.8–11, preferably pH 7.0–9.5) within about 30–60 min. and moderate temperatures (4°–40° C). Additionally, the agents are soluble in a variety of organic solvents, thus being useful and important in the coupling of low molecular weight, partially protected peptides and other biologically useful ligands.

The PEG does not have to be of a particular molecular weight, but it is preferred that the molecular weight be between 500 and 40,000; more preferably between 2,000 and 20,000. The choice of molecular weight of PEG is made based on the nature of the particular protein employed, for example, the number of amino groups available for modification.

The N-hydroxysuccinimide released during protein modification is non-toxic material that is often used in protein chemistry, especially for preparation of biologically active protein-adducts. As in the case of above mentioned carbonyldiimidazole activated PEG and PEG-phenylcarbonates, the product of protein modification using SC-PEG or BSC-PEG has PEG-chains grafted onto the polypeptide backbone through carbamate (urethane) linkages. However, due to the higher reactivity of the new agents, higher degrees of modification are achievable in shorter periods of time. An additional advantage of succinimide carbonate activated PEG is that those active functional groups that do not react with amino groups of a protein undergo fast aqueous hydrolysis producing N-hydroxysuccinimide, carbon dioxide and hydroxy-terminated PEG. This is of particular importance in the case of bifunctional PEG derivatives (BSC-PEG). These materials can serve a dual purpose: PEGylation and crosslinking at the same time. The BSC-PEG, like any homobifunctional material can be used to crosslink two different proteins. When a BSC-PEG molecule reacts with a protein via only one end group, the other SC-group of the polymer, which does not react with the amine, is hydrolyzed and therefore no extraneous (potentially antigenic) residues are introduced onto the PEG-protein conjugate.

Biological activities of proteins modified with SC-PEG and BSC-PEG are preserved to a large extent as shown by the examples below. There is one literature precedent in which protein (tissue plasminogen activator) covalently conjugated with PEG via urethane links had a higher specific activity than the same protein modified with SS-PEG to approximately the same extent [Berger & Pizzo, Blood, 71, 1641–1647, 1988].

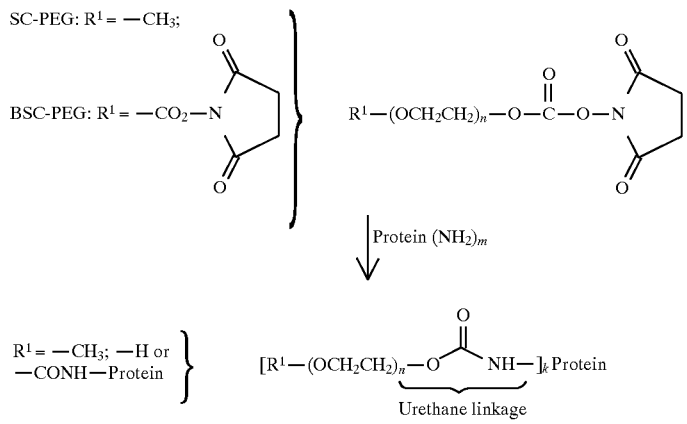

Naturally, the utility of SC-activated PEG-derivatives extends to preparation of PEG-conjugates of low molecular weight peptides and other materials that contain free amino groups.

A one-pot procedure for introduction of SC-groups onto PEG was developed (Scheme 3 below). First, polyethylene glycol chloroformate was generated in situ by treatment of the polymer (PEG) with phosgene. The resulting chloroformate was then reacted with N-hydroxysuccinimide (HOSU) followed by triethylamine (TEA) to yield the desired activated derivatives of PEG. The activated polymer preparations were purified from low molecular weight materials and determined to contain the theoretical amounts of active groups.

Scheme 3: Synthesis of N-succinimide carbonate derivatives of poly(ethylene glycol).

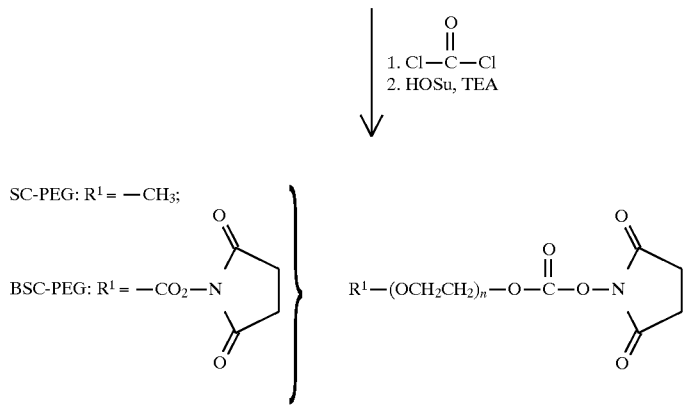

EXAMPLE 1

Preparation of SC-PEG: Methoxypolyethylene glycol of molecular weight 5000 (Union Carbide, 60 g, 12 mmol) was dissolved in toluene/dichloromethane (3:1, 200 ml) and treated with a toluene solution of phosgene (30 ml, 57 mmol) overnight. The solution was evaporated to dryness and the remainder of phosgene was removed under vacuum. The residur was redissolved in toluene/dechloromethane (2:1, 150 ml) and treated with solid N-hydroxysuccinimide (2.1 g, 18 mmol) followed by triethylamine (1.7 ml, 12 mmol). After 3 hours, the solution-was filtered and evaporated to dryness. The residue was dissolved in warm (50° C.) ethyl acetate (600 ml), filtered from trace insolubles and cooled to facilitate precipitation of the polymer. The product was collected by filtration and then recrystallized once more from ethylacetate. The product was dried in vacuo over $P_2O_5$. The yield was 52.5 g (85% of theory).

To determine the active carbonate content of the product, samples of the polymer were reacted with a measured amount of benzylamine in dichloromethane and the excess of amine was titrated with perchloric acid in dioxane. These titrations indicated that 1 g of the product contained $1.97 \times 10^{-4}$ mole of active carbonate (101% of theoretical content). I.R. (film on NaCl, $cm^{-1}$) characteristic bands at : 1812 and 1789 (both C=O, succinimide); 1742 (C=O, carbonate); 1114 ($CH_2OCH_2$). $^{13}C$—NMR ($CDCl_3$) : δ 168.5 ($CH_2C=O$); 151.3 (O—$CO_2$); 71.9 ($CH_3OCH_2$) 70.2 (PEG); 68.7 ($CH_2CH_2OCO_2$); 68.0 ($CH_2CH_2OCO_2$); 58.9 ($CH_3O$); 25.2 ($CH_2C=O$) ppm .

EXAMPLE 2

Preparation of BSC-PEG: Polyethylene glycol of molecular weight 4600 (Union Carbide, 50g, 21.7 mequiv. OH) was converted to the corresponding bis-N-hydroxysuccinimide carbonate using a toluene solution of phosgene (50 ml, 96.5 mmol) and then N-hydroxysuccinimide (3.8 g, 23 mmol) and triethylamine (3.2 ml, 23 mmol) following the procedure described in Example 1. After purification the product was obtained as a white powder (51 g, 96%). Active carbonate content was $4.0 \times 10^{-4}$ mole/g (98% of theoretical) as determined by titrations with benzylamine-perchloric acid. I.R. (film on NaCl, $cm^{-1}$) characteristic bands at : 1812 and 1789 (both C=O, succinimide); 1742 (C↑O, carbonate); 1114 ($CH_2OCH_2$). $^{13}C$—NMR($CDCl_3$): δ 168.5 ($CH_2C=O$); 151.3 (O—$CO_2$); 70. 2 (PEG); 68. 7 ($CH_2CH_2OCO_2$); 68.0 ($CH_2CH_2OCO_2$); 25.2 ($CH_2C=O$) ppm. H-NMR ($CDCl_3$) : δ 4.35 (m, 4H, $CH_2OCO_2$); 3.55 (s, ~400H, PEG); 2.74 (s, 8H, $CH_2C=O$) ppm.

EXAMPLE 3

Preparation of polyethylene glycol-Bovine Serum Albumin conjugates (PEG-BSA):

A. SC-PEG (1 g) was added to a stirred solution of Bovine Serum Albumin (BSA) (100 mg) in 0.1M sodium phosphate, pH 7.8 (20 ml). Sodium hydroxide (0.5N) was used to maintain pH 7.8 for 30 min. The excess of free PEG was removed by diafiltration using 50 mM phosphate buffered saline. The extent of modification of BSA was approximately 50% (30 amino groups of BSA out of total 60 reactive with SC-PE) as determined by trinitrobenzenesulfonate (TNBS) titration of amino groups [Habeeb, Analyt. Biochem. 14, 328–336 (1966)].

The same degree of modification was obtained when the experiment was repeated under identical conditions using SS-PEG instead of SC-PEG.

B. SC-PEG (1 g) was added to a stirred solution of BSA (100 mg) in 0.1M sodium borate, pH 9.2. Sodium hydroxide (0.5N) was used to maintain pH 9.2 for 30 min. The excess of free PEG was removed by diafiltration and the product assayed for the number of free amino groups. Approximately 68% (41) of the amino groups of the native BSA were modified.

C. BSC-PEG (1 g) was added to a stirred solution of BSA (100 mg) in 0.1M sodium borate, pH 9.2. Sodium hydroxide (0.5N) was used to maintain pH 9.2 for 30 min. The excess of free PEG was removed by diafiltration and the product assayed for the number of free amino groups. Approximately 80% (48) of the amino groups of the native BSA were modified. Analysis of the product by HPLC (Gel Filtration) indicated that over 65% of PEG-BSA was in intermolecularly crosslinked form and about 35% of the product had the same molecular weight as PEG-BSA from Example 3B.

EXAMPLE 4

Preparation of PEG-glutaminase: A solution of glutaminase Pseudomonas 7A (200 mg) in 0.1M sodium phosphate, pH 7.8 was treated with SC-PEG (4.7) g). The solution was stirred and pH 7.8 was maintained for 30 minutes. The excess free PEG was removed by diafiltration using 50 mM PBS. The extent of modification of glutaminase was 74% as determined by trinitrobenzenesulfonate titration of amino groups (see Habeeb, 1966 above). The PEG-glutaminase product preserved 81% of the enzymatic activity of the parent glutaminase.

EXAMPLE 5

Preparation of PEG-Trypsin: A solution of bovine pancreatic trypsin (Boeringer-Mannheim, 120 mg in 20 ml), that was dialyzed overnight at 4° C. against 20 mM $CaCl_2$ in 1 mM HCl, was brought to 25°C. and treated with SC-PEG (600 mg) for 30 min. During this time pH 7.8 was maintained in the reaction vessel by automatic titration with 0.5N NaOH. The solution was acidified to pH 3 and extensively diafiltered to remove excess of free polymer using 20 mM $CaCl_2$ in 1 mM HCl as a replacement fluid. The modified trypsin had approximately half of the free amino groups of the parent enzyme (7 PEG chains per trypsin molecule) as determined by TNBS titration of amino groups (Habeeb 1966). The PEG-trypsin product preserved 96% of enzymatic activity of the parent enzyme towards Nα-benzoyl-L-arginine ethyl ester.

EXAMPLE 6

Preparation of PEG-Arginase: A solution of bovine liver arginase (Sigma, 90 mg) in 0.1M NaCl (20 ml) was treated with SC-PEG (1.3 g) at 27°C. while pH 8.0 was maintained by automatic titration with 0.5N NaOH. After 30 min. the reaction mixture was diafiltered using 50 mM PBS as a replacement fluid. Approximately 64% of the amino groups of the native arginase were modified (56 PEG chains per arginase molecule). The PEG-arginase product retained 70% of specific activity of the native enzyme when assayed with 2,3-butanedione (BUN-urea reagent) at pH 9.5.

EXAMPLE 7

Other polypeptides, including chymotrypsin, asparaginase, and adenosine deaminase, have been modified with SC-PEG using the procedures set forth herein.

The methods of using SC- and/or BSC-functionalized polyalkylene oxides, such as PEG and its copolymers are generally applicable to the preparation of other modified polypeptides and other biologically active components having amino groups.

While the present invention has been described by reference to N-hydroxysuccinimide derivatives, it will be obvious to those skilled in the art that other N-hydroxydicarboximides may be substituted therefor. Typical of such derivatives are N-hydroxyphthalimide, N-hydroxyglutarimide, N-hydroxytetrahydrophthalimide, N-hydroxy-5-norbornene-2,3-dicarboximide or other N-disubstituted derivatives of hydroxylamine.

EXAMPLE 8
Comparison of SC-PEG to SS-PEG

Figure 1:
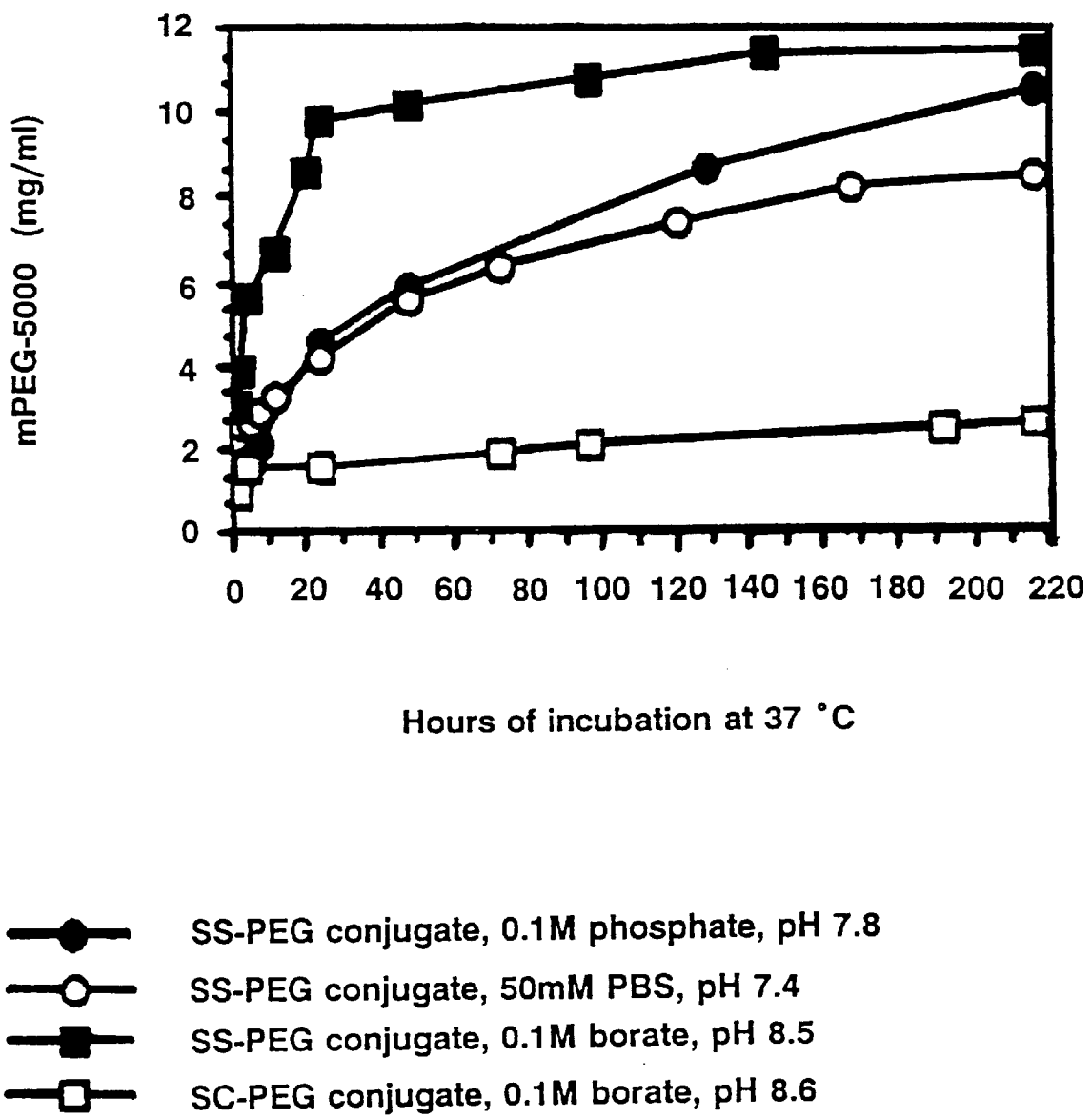
FIG. 1. Release of mPEG from PEG-BSA conjugates. Experimental Conditions

A. As seen in Scheme 2, the product of protein modification using SC-PEG has PEG-chains grafted onto the polypeptide backbone through carbamate (urethane) linkages. Greater stability of the urethane linkage relative to the ester bond produced upon use of SS-PEG (see Scheme 1) was expected to prove a key difference between the two activated PEG's and the corresponding PEG-protein conjugates. Our studies indeed confirmed this expectation. FIG. 1 shows the results of GF-HPLC measurements of the amounts of free mPEG produced as a result of incubation of PEG-BSA conjugates derived from each of the activated PEG's. Considerably higher stability of the SC-PEG-derived conjugate is apparent.

B. To estimate the reactivities of SC-PEG and SS-PEG, kinetic measurements of hydrolysis of the activated polymers in phosphate buffer and their aminolysis by Nα-acetyl-lysine (NAL) were performed. The results of these experiments are summarized in Table 1. It is clear from these data that SS-PEG is a more reactive reagent than SC-PEG. The difference in hydrolysis rates was larger than the difference in aminolysis rates; consequently, SC-PEG showed more favorable $K_{am}/K_h$ ratios. The slower hydrolysis of SC-PEG was also manifested in superior storage stability of the reagent (FIG. 2).

C. Reactivity of the activated PEGs as a function of pH was determined using NAL as a model for the ε-amino group of a protein. Each of the activated PEGs was reacted with an equimolar amount of NAL at different pH's, and measured the unreacted NAL using the TNBS-assay (FIG. 3). The optimal pH for use of SC-PEG was found to be about 9.3. It is not advisable to use SS-PEG at pH>8.0, due to the limited stability of PEG-succinate ester. However, even at pH values less than 8.0 this activated PEG was found to be very reactive.

D. Both reagents showed high reactivity towards Trypsin yielding comparably modified enzyme derivatives in mild conditions (pH 7.5–8.5) within 30 min. The products were purified by diafiltration, and the degrees of modification were determined by fluorometric assay, according to Stocks, et al. (1986) Anal. Biochem. 154, 232.

All PEG-modified trypsin derivatives were essentially lacking (<1% of native) proteolytic activity as determined by the Azocoll assay [Chavira, et al. (1984) Anal. Biochem. 136, 446]. The specific activities of representative SS-and SC-PEG modified trypsins towards low molecular weight substrates are summarized in Table 2. The modifications produced hardly any changes in esterolytic activities towards benzoyl-L-arginine ethyl ester, but did enhance the activities towards p-nitroanilides. Michaelis-Menten kinetic constants for several SC- and SS-PEG modified trypsins were measured using ZAPA as the substrate. These results, summarized in Table 3, indicate that, while $V_{max}$, $K_{cat}$ and $K_{cat}/K_m$ were increasing gradually with the extent of modificaitons, $K_m$ values were decreasing.

As compared to SS-PEG, SC-PEG is a less reactive yet more. selective reagent. This is evidenced by its higher $K_{am}/K_h$ ratios and better storage stability. SC-PEG is a sufficiently reactive reagent to produce PEG-protein conjugates under mild conditions within 30 min. SC-PEG can be used in a broader pH range than SS-PEG, showing the highest reactivity at pH=9.3. PEG-protein conjugates obtaining through use of SC-PEG are chemically more stable than SS-PEG derived conjugates. The PEG-Trypsin conjugates produced by both activated PEG's have very similar properties: They show no proteolytic activity, well preserved esterolytic activity, and dramatically increased activity towards p-nitroanilide substrates. Michaelis-Menten constants of the modified enzymes indicate that the attachment of PEG to trypsin causes an increase in both the rate of turnover of ZAPA and its affinity towards the modified enzymes.

TABLE 1

Comparison of first order rate constants for hydrolysis ($K_h$) and aminolysis ($K_{am}$) of SC-PEG and SS-PEG[a]

| pH | Temp. (°C.) | Hydrolysis: $K_h^b$(min$^{-1}$) × $10^3$ and [$t_{1/2}$(min)] | | Aminolysis: $K_{am}^c$(min$^{-1}$) × $10^3$ and [$K_{am}/K_h$] | |
|---|---|---|---|---|---|
| | | SC-PEG | SS-PEG | SC-PEG | SS-PEG |
| 7.0 | 4  | 0.87 [793] | 1.84 [376] | 2.64 [3.0] | 3.74 [2.0] |
|     | 27 | 6.05 [115] | 10.4 [67]  | 26.4 [4.4] | 41.4 [4.0] |
|     | 37 | 14.2 [49]  | 25.9 [27]  | 81.7 [5.8] | 104 [4.0] |
| 7.4 | 22 | 5.37 [129] | 10.7 [65]  | 29.1 [5.4] | 42.7 [4.0] |
|     | 27 | 9.0 [77]   | 16.0 [43]  | 48.6 [5.4] | 73.6 [4.6] |
|     | 37 | 19.3 [36]  | 37.6 [18]  | 145 [7.5]  | 193 [5.1] |
| 7.8 | 4  | 1.37 [505] | 2.58 [268] | 12.4 [9.1] | 15.0 [5.8] |
|     | 27 | 10.3 [67]  | 21.6 [32]  | 130 [12.6] | 152 [7.0] |
|     | 37 | 21.8 [32]  | 48.8 [14]  | 226 [10.6] | 267 [5.5] |

[a]All the measurements were performed by following the appearance of N-hydroxysuccinimide anion (—OSu) at 260 nm in 0.008M sodium phosphate; concentration of PEG-bound succinimidyl active acyl at time zero [SX-PEG]$_0$ was 0.1 mM; in aminolysis experiments concentration of N$^\alpha$-acetyl-lysine at time zero [NAL]$_0$ was 3 mM.
[b]$K_h$ = Rate$_h$/[SX-PEG]$_0$, where Rate$_h$ = dA$_{260}$/dt × 1 E$_{260}$ × 1F; $\epsilon_{260}$ = 8500M$^{-1}$ cm$^{-1}$ is an extinction coefficient of —OSu; and F = [—OSu]/([HOSu] + [—OSu]) = (1 + 10$^{6.0\text{-pH}}$)$^{-1}$.
[c]$K_{am}$ = Total Rate/[SX-PEG]$_0$ − $K_h$. The Total Rate in aminolysis experiments was calculated the same way as Rate$_h$ in hydrolysis experiments.

TABLE 2

SUMMARY OF MODIFICAITON, ESTEROLYTIC ACTIVITY, AND AMIDOLYTIC ACTIVITY DATA FOR TYPSIN AND ITS mPEG DERIVATIVES

| Trypsin Derivatives[a] | Modif[b] (%) | BAEE[c] ($\mu$/mg) | % Native | BAPA[d] ($\mu$/mg) | % Native | ZAPA[d] ($\mu$/mg) | % Native |
|---|---|---|---|---|---|---|---|
| Native Trypsin | 0 | 92.4 | 100 | 1.26 | 100 | 7.81 | 100 |
| SC-PEG$_N$-Trypsin | | | | | | | |
| N = 6  | 42.3 | 103  | 112  | 2.26 | 179 | 15.3 | 196 |
| N = 7  | 45.8 | 87.9 | 95.1 | 2.38 | 188 | 17.5 | 224 |
| N = 9  | 58.8 | 90.1 | 97.5 | 2.67 | 212 | 18.9 | 242 |
| N = 12 | 77.9 | 85.1 | 92.2 | 3.83 | 304 | 25.5 | 326 |
| SS-PEG$_N$-Trypsin | | | | | | | |
| N = 7  | 44.8 | 102  | 110  | 3.25 | 258 | 18.8 | 241 |
| N = 12 | 770  | 94.3 | 102  | 4.34 | 344 | 24.7 | 316 |

[a]For SX-PEG$_h$-Typsin, N = 15 × (% Modif)/100 and is rounded to the nearest integer.
[b]The percent of amino groups modified was determined by the fluorescamine assay [Stocks, et al. (1986) Anal. Biochem. 154, 232].
[c]The BAEE (N$^\alpha$-benzoyl-L-arginine ethyl ester) trypsin assay was done at pH 7.8, 37° C. w/ a substrate conc'n of 0.5 mM. The extinction coefficient was $\epsilon_{253}$ = 808M$^{-1}$ cm$^{-1}$ [Kezdy, et al. (1965) Biochemistry 4, 99].
[d]The BAPA (N$^\alpha$-benzoyl-D, $\gamma$ L-arginine-p-nitroanilide) and ZAPA (N$^\alpha$-CBZ-L-arginine-p-nitroanilide) amidolytic assays were done w/ a substrate conc'n of 1 mM in 50 mM Tris-HCl pH 8.1, 10 mM CaCl$_2$, at 37° C. The extinction coefficient for p-nitroaniline, $\epsilon_{410}$ = 8800M$^{-1}$ cm$^{-1}$, was used in both assays.

TABLE 3

MICHAELIS-MENTEN CONSTANTS FOR THE AMIDOLYTIC ACTIVITY OF NATIVE TRYPSIN AND ITS mPEG DERIVATIVES[a]

| Trypsin Derivatives | Km (mM) | V$_{max}$ ($\mu$M/min) | K$_{cat}$ (min$^{-1}$) | Kcat/Km (mM$^{-1}$ · min$^{-1}$) |
|---|---|---|---|---|
| Native Trypsin | 1.08 | 15.7 | 378 | 349 |
| SC-PEG$_N$-Trypsin | | | | |
| N = 7  | 0.29 | 19.6 | 470 | 1626 |
| N = 9  | 0.21 | 20.2 | 484 | 2290 |
| N = 12 | 0.11 | 22.9 | 549 | 4973 |
| SS-PEG$_h$-Trypsin | | | | |
| N = 7  | 0.21 | 18.6 | 447 | 2172 |
| N = 12 | 0.13 | 22.5 | 539 | 4159 |

[a]The measurements took place at 37° C. with a constant trypsin protein concentration of 1.0 $\mu$g/ml (via Bluret assay). N$\alpha$-carbobenzoxy-L-arginine-p-nitroanilide (ZAP) was used as a substrate in concentrations varying from 0.02 to 1.71 mM in 50 mM Tris-HCl pH 7.8, 10 mM calcium chloride. The constants were calculated from Lineweaver-Burk plots of the initial rates of the appearance of p-nitroaniline ($\epsilon_{410}$ = 8800M$^{-1}$ cm$^{-1}$).

What is claimed is:

1. A process for preparing a polyalkylene oxide having a terminal oxycarbonyl-oxy-N-dicarboximide group, which comprises a) treating a polyalkylene oxide with phosgene to form a polyalkylene oxide chloroformate in situ:

b) reacting said polyalkylene oxide chloroformate with an N-hydroxy-N-dicarboximide followed by a base to form a polyalkylene oxide having a terminal oxycarbonyl-oxy-N-dicarboximide group.

2. The process of claim 1, wherein the N-hydroxy-N-dicarboximide is N-hydroxysuccinimide.

3. The process according to claim 1 wherein the base is triethylamine.

4. The process of claim 1 wherein said polyalkene oxide having said oxycarbonyl-oxy-N-dicarboximide has the structure:

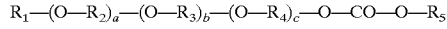

wherein R$_1$ is H—, H$_3$C— or a carbonyl-oxy-N-dicarboximide group;

R$_2$, R$_3$, and R$_4$ are independently selected from the group consisting of straight and branched alkyl groups;

R$_5$ is an N-dicarboximide group; and

α is and integer between 1 and 1,000 and b and c are independently zero or an integer between 1 and 1,000.

5. The process of claim 4 wherein R$_2$, R$_3$, and R$_4$ are independently selected from the group consisting of —CH$_2$—CH$_2$—, —CH$_2$—CH(CH$_3$)—, and —CH$_2$CH$_2$CH$_2$CH$_2$—.

6. The process of claim 4 wherein R$_1$ and R$_5$ are carbonyl-oxy-N-dicarboximide groups and the N-dicarboximide of R$_1$ and R$_5$ are independently selected from the group consisting of N-succinimide, N-phthalide, N-glutarimide, N-tetrahydrophthalimide and N-norborene-2,3-dicarboximide groups.

7. The process of claim 4 wherein R$_5$ is an N-succinimide group.

8. The process of claim 4 wherein said polyalkene oxide having said oxycarbonyl-oxy-N-dicarboximide has the structure:

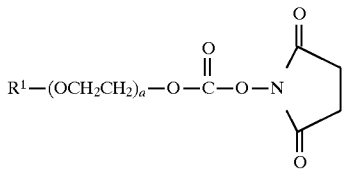

wherein R$_1$ is H$_3$C— or H— and (α) is an integer between 1 and 1,000.

9. The process of claim 4 wherein said polyalkene oxide having said oxycarbonyl-oxy-N-dicarboximide has the structure:

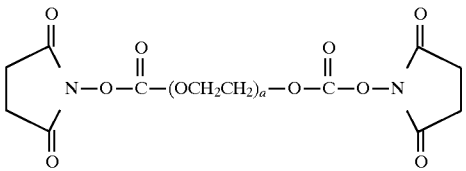

wherein (α) is an integer between 1 and 1,000.

10. The process of claim 1, wherein said polyalkylene oxide has a molecular weight from about 500 to about 40,000.

11. The process of claim 10, wherein said polyalkylene oxide has a molecular weight from about 2,000 to about 20,000.

12. The process of claim 11, wherein said polyalkene oxide has a molecular weight about 5,000.

13. The process of claim 1, wherein said polyalkylene oxide having said terminal oxycarbonyl-oxy-N-dicarboximide group is polyethylene glycol-succinidyl carbonate.

14. The process of claim 1, wherein said polyalkylene oxide having said terminal oxycarbonyl-oxy-N-dicarboximide group is polyethylene glycol-bis-succinidyl carbonate.

* * * * *